United States Patent [19]
Gabriel

[11] Patent Number: 5,614,675
[45] Date of Patent: Mar. 25, 1997

[54] SYSTEM AND METHOD FOR USING PHASE DIFFERENCES TO MEASURE THE THICKNESS OF AN OPTICAL ELEMENT

[75] Inventor: Fred C. Gabriel, Stamford, Conn.

[73] Assignee: Hughes Aircraft Company, Los Angeles, Calif.

[21] Appl. No.: 165,432

[22] Filed: Dec. 10, 1993

[51] Int. Cl.$^6$ .................................................. G01N 29/00
[52] U.S. Cl. .................................. 73/597; 73/602; 73/629
[58] Field of Search ........................... 73/630, 602, 629, 73/597, 601; 364/508

[56] References Cited

U.S. PATENT DOCUMENTS

| | | | |
|---|---|---|---|
| 2,484,623 | 10/1949 | Heising | 73/630 |
| 3,237,445 | 3/1966 | Wood | 73/630 |
| 3,595,069 | 7/1971 | Fowler | 73/579 |
| 3,741,334 | 6/1973 | Kaule | 73/630 |
| 4,062,227 | 12/1977 | Heyman | 73/630 |
| 4,624,142 | 11/1986 | Heyman | 73/597 |
| 4,875,175 | 10/1989 | Egee | 73/601 |
| 5,052,227 | 10/1991 | Le Floc'H et al. | 73/597 |

Primary Examiner—Christine K. Oda
Attorney, Agent, or Firm—W. C. Schubert; W. K. Denson-Low

[57] ABSTRACT

A system and technique for measuring the thickness of an optical element. A first energy signal of a first phase is transmitted into the element. The first signal reflects off of a distal surface of the element and is detected as a return signal. The phase of the reflected signal is compared to the phase of the transmitted signal and the frequency varied to extract a third signal representing a desired phase difference therebetween. Corresponding frequency data are processed to determine the thickness of the element at the point of transmission of the first signal.

7 Claims, 4 Drawing Sheets

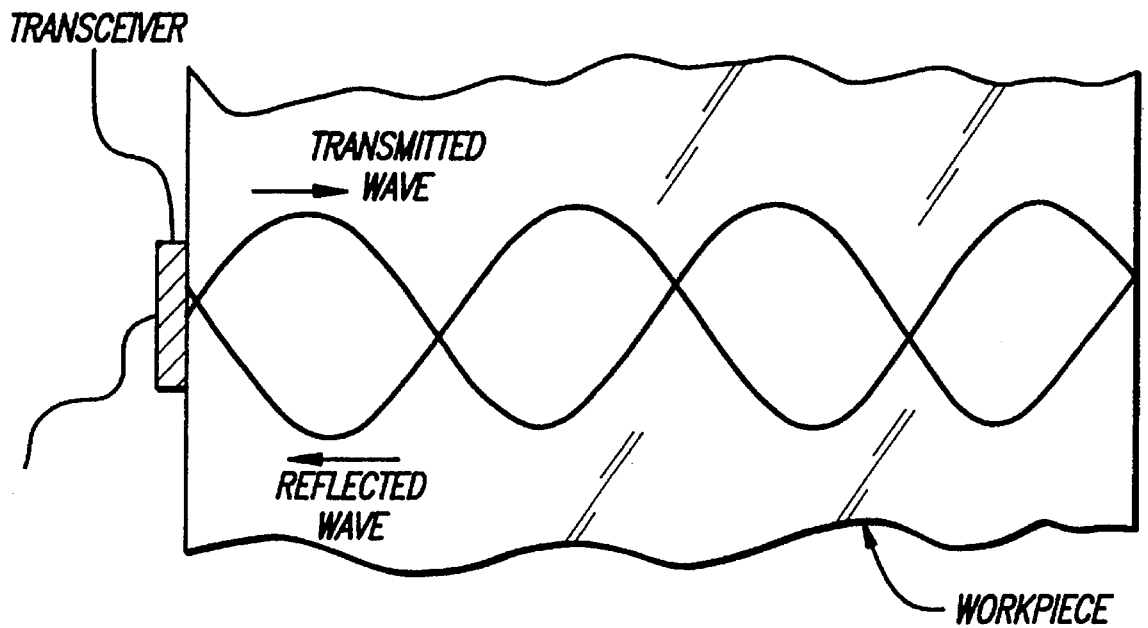
FIG. 4
FIG. 5
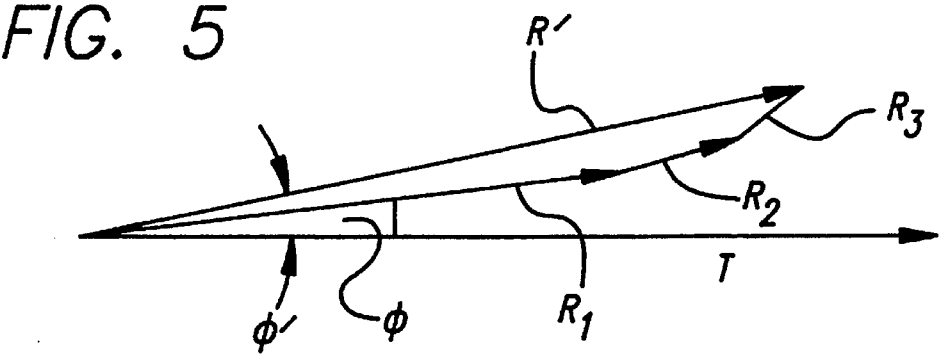
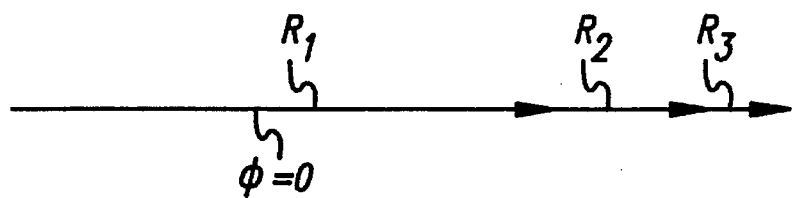
FIG. 6

SYSTEM AND METHOD FOR USING PHASE DIFFERENCES TO MEASURE THE THICKNESS OF AN OPTICAL ELEMENT

BACKGROUND OF THE INVENTION

1. Field of the Invention

The present invention relates to systems and techniques for measuring the thickness of solid objects. More specifically, the present invention relates to systems and techniques for measuring the surface contour of precision mirrors.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

2. Description of the Related Art

In many applications, there is a need for an optical element which has been manufactured to precise tolerances. In large telescopes, for example, large mirrors are required for which precision in the figure thereof is critical. The figure of a mirror is the contour of the working surface. The contour of the working surface determines the extent to which the mirror can accurately focus an image in a specific image plane.

Conventional techniques for measuring the figure of the mirror include mechanical gaging and optical interferometry. With the first mentioned technique, the nonworking surface is often planar such that the contour of the working surface may be determined with multiple thickness measurements thereon. This approach is of limited accuracy and better suited to the early and more approximate phases of mirror figuring. It is also cumbersome in that it requires interruption of the grinding or polishing to accommodate the measuring fixtures on the working surface.

Optical interferometry involves the illumination of the surface of the mirror with coherent light and analysis of an interference pattern created when light reflected off the mirror intersects a reference beam. This technique offers high accuracy, but requires an elaborate setup, and is better suited to the final phases of mirror figuring.

Yet another technique involves the use of ultrasonic ranging to measure the mirror surface in terms of the time delay required for a transmitted pulse to traverse the mirror thickness from the front, be reflected off the back, and traverse the mirror thickness again to be detected as an echo.

Conventional ultrasonic ranging systems generally use rectangular pulses with concomitant demands for short pulse rise time and wide circuit and transducer bandwidth to achieve accuracy. For example, the optical material Zerodur transmits sound at a velocity of 7.6 kilometers per second. Thus, to gage the material to a precision of 1 micrometer, a typical requirement for coarse gaging, requires measurement of the pulse edge timing to $1(10)^{-6}/7.6(10)^3 = 0.13$ nanoseconds, a difficult requirement.

Thus, there is a need in the art for simple, low cost, precise system and technique for measuring the surface contour of optical elements, particularly, large telescope mirrors.

SUMMARY OF THE INVENTION

The need in the art is addressed by the present invention which provides a system and technique for measuring the thickness of an optical element. In a most general implementation, the invention is adapted to transmit a first continuous wave (cw) signal of a first phase into the element. The first signal reflects off of a distal surface of the element and is detected as a return signal. The phase of the reflected signal is compared to the phase of the transmitted signal to extract a third signal representing a phase difference therebetween. This phase difference signal is processed to determine the thickness of the element at the point of transmission of the first signal.

The invention thus provides a simple, low cost, precise system and technique for measuring the surface contour of optical elements, particularly, large telescope mirrors.

BRIEF DESCRIPTION OF THE DRAWINGS

FIG. 4 is a simplified representation of a wave propagating through the work piece.

FIG. 5 is a phasor representation of the propagation of the wave through the work piece.

FIG. 6 is a phasor representation of the propagation of the wave through the work piece with zero or 360 degrees phase shift.

DESCRIPTION OF THE INVENTION

Illustrative embodiments and exemplary applications will now be described with reference to the accompanying drawings to disclose the advantageous teachings of the present invention.

Figure 1:
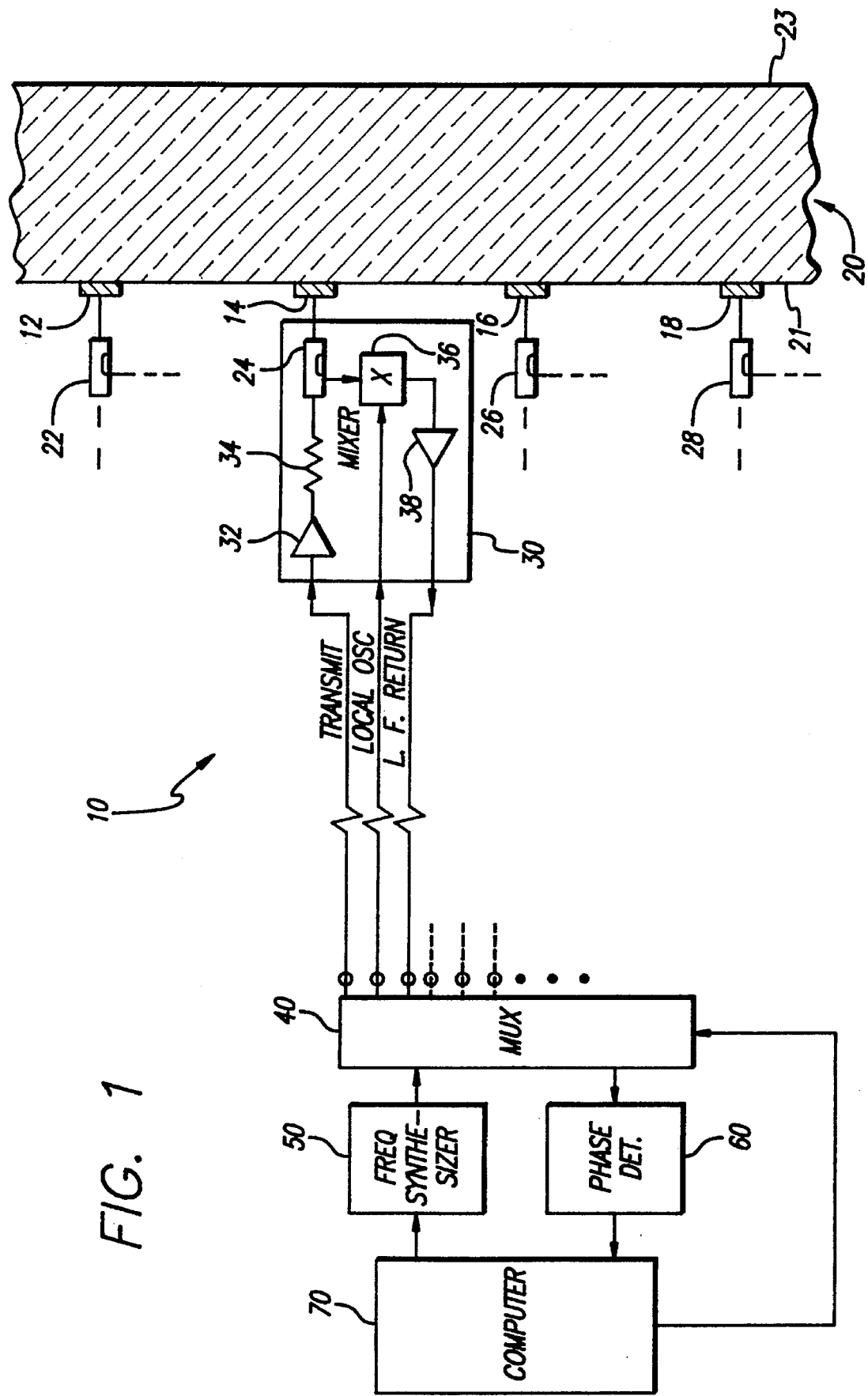
FIG. 1 is a block diagram of a system for measuring the thickness of an optical element designed in accordance with the teachings of the present invention.

FIG. 1 is a block diagram of a system 10 for measuring the thickness of a work piece 20 designed in accordance with the teachings of the present invention. The work piece 20 may be a large telescope mirror, a lens or other solid optical element. The work piece 20 has a proximal first working surface 21 and a planar distal second surface 23. The system 10 includes an array of piezoelectric transducers 12, 14, 16 and 18 deployed over the working surface 21 of the work piece 20. The transducers are of conventional design and construction. In practice, the transducers would be deployed at over the entire working surface 21 of the work piece 20 to facilitate the determination of the surface contour thereof.

Each transducer 12, 14, 16 and 18 is connected to an associated directional coupler 22, 24, 26 and 28 respectively. Each coupler is a component of a remote terminal circuit. While only one remote terminal circuit 30 is shown, it is understood that each transducer is driven by an identical remote terminal circuit. Each remote terminal circuit further includes an amplifier 32 which drives a continuous sinewave (cw) transmit signal, such as an acoustic signal, into the transducer via a resistor 34 and the associated directional coupler (e.g., 24). In the illustrative embodiment, the frequency of the transmit signal is in a range sufficient to cause the transducer to vibrate at a frequency which induces an ultrasonic vibration into the work piece 20 which is reflected off of the second surface 23 thereof. As discussed more fully below, the reflected signal is sensed by the transducer 14 and coupled to a mixer 36 by the directional coupler 24. The transmit signal is supplied by a programmable frequency synthesizer 50 through a multiplexer 40 under control of a computer 70. A local oscillator signal is supplied by the frequency synthesizer 50 to a mixer 36. The local oscillator signal allows the mixer 36 to downconvert the received signal to a low frequency return signal. This signal is amplified by a second amplifier 38 and sent a phase detector 60 via the multiplexer 40.

Figure 2:
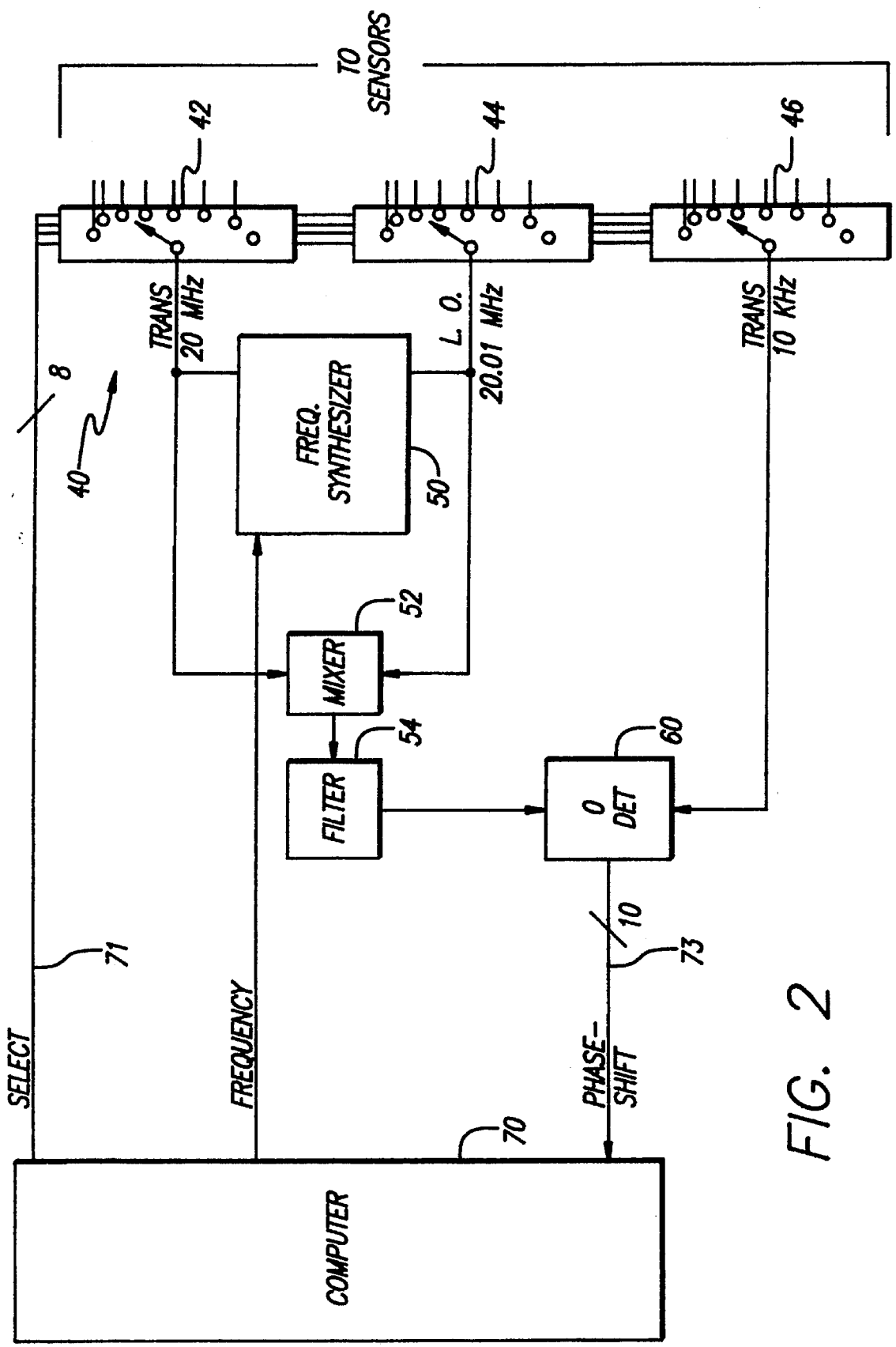
FIG. 2 is a block diagram showing the multiplexer and signal processing circuitry of the system of FIG. 1.

The multiplexer 40, the frequency synthesizer 50 and the phase detector 60 comprise a base unit as shown in greater detail in the block diagram of FIG. 2. The multiplexer 40 is implemented with three parallel multiplexers 42, 44 and 46 each of which is controlled by the computer 70 via a select bus 71. The first multiplexer 42 provides the transmit signal to each of the remote circuits 30, the second multiplexer 44 provides the local oscillator signal to each of the remote circuits 30, and the third multiplexer 46 provides the low frequency return signal from each of the remote circuits 30.

The transmit signal is input to the first multiplexer 42 and the local oscillator signal is input to the second multiplexer 44 by the frequency synthesizer 50. The transmit signal is downconverted by the local oscillator signal by a mixer 52. The downconverted transmit signal is filtered by a filter 54 and input to the phase detector 60 as a reference signal. The second input to the phase detector 60 is provided by the common output of the third multiplexer 46. The phase detector 60 provides a digital output to the computer 70 via a bus 73.

The computer analyzes the phase shift in the return signal and computes the thickness of the work piece at each of the plurality of locations of the transducers as discussed more fully below.

Figure 3:
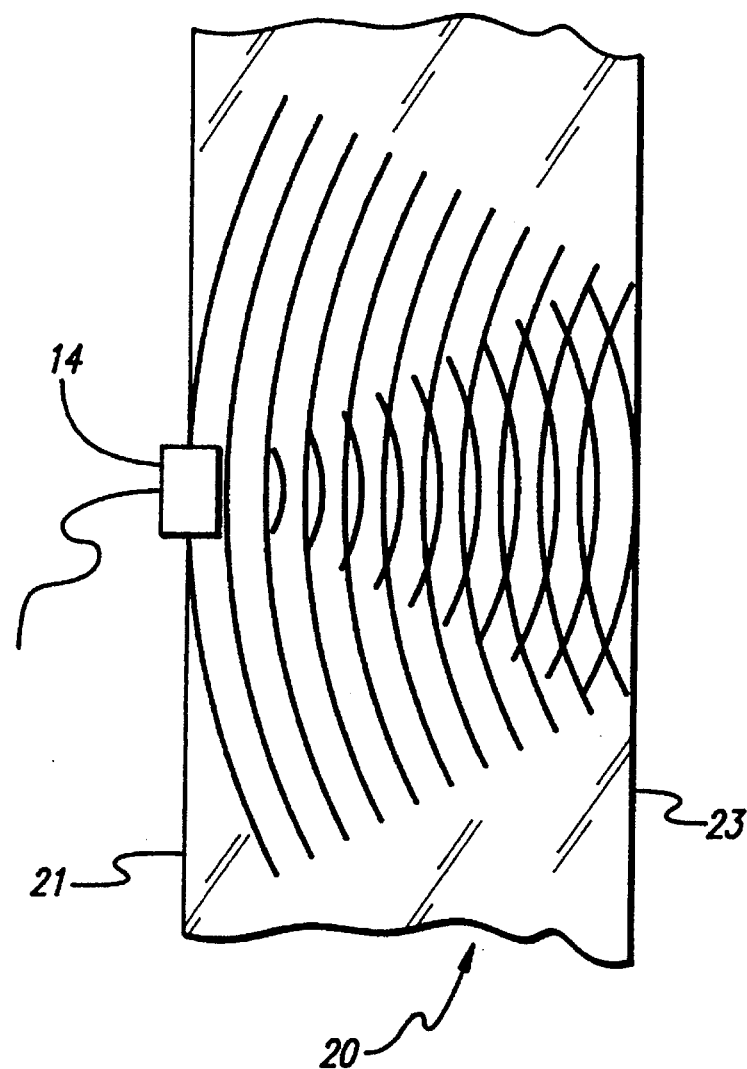
FIG. 3 depicts the propagation of an ultrasonic wave through the work piece.

FIG. 3 depicts the propagation of an ultrasonic wave through the work piece. Reflected from the distal surface 23, the return wave produces an output from the transducer 14 superimposed upon the transmitted continuous sinewave signal. The round trip time delay causes a phase-shift of the return wave with respect to the transmitted wave (and of their electrical signals) which is a measure of the material thickness.

This is shown in FIG. 4 which is a simplified representation of a wave propagating through the work piece.

FIG. 5 is a phasor representation of the propagation of the wave through the work piece. In FIG. 5, T and $R_1$ are the phasors representing transmitted and received waves, respectively, with a phase-shift, $\phi$, therebetween. In such a system, one degree of phase-shift might, for example, represent one micron of thickness. The range of measurement would then be 360 microns without ambiguity. Thus, if a machining operation were to remove 1 micron of glass, the output of a phase detector comparing transmitted and received waves would change by one degree. In practice, however, as evidenced by pulsed ranging systems, second and third round trip echoes are also present in appreciable amounts. As shown in FIG. 5, these are of reduced amplitude and phased in integer multiples of the desired phase shift $\phi$. The effect of the second and third round trip echoes is to produce a resultant, R' having a phase shift $\phi'$ altered from $\phi$.

Figure 7:
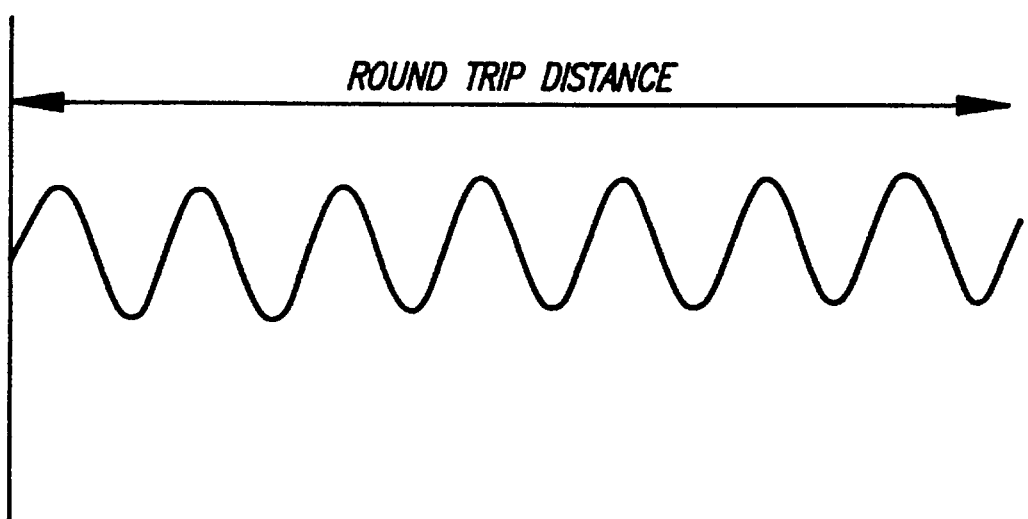
FIG. 7 is a simplified representation of a wave propagating through the work piece showing an integral number of wavelengths where the path is unfolded for clarity.

However, as shown in FIG. 6, this disturbance is absent in the simple case of zero or 360 degrees phase shift. In this case, all the received phasors are colinear. (This effect is also present for the case of 180°, as will be explained later.) The present invention exploits this effect. The condition of zero phase-shift between transmit and receive signals is present only when a unique condition is satisfied: that is, that there is an integral number of sound wavelengths contained in the round trip ranging path, as depicted in FIG. 7 where the path has been unfolded for clarity.

In accordance with the present teachings, the computer 70 adjusts the frequency of the signal transmitted by the frequency synthesizer 50 until there is a zero degree phase shift or phase difference between transmitted and received signals. This corresponds to an integral number of wavelengths in the round trip measuring path. Next, the frequency is gradually increased until the next phase-null occurs corresponding to an increase by one in the number of wavelengths in the path. The number of wavelengths in the path at the frequency 'f' of the first null is equal to the frequency 'f' divided by the frequency change $\Delta f$ or $f/\Delta f$. The corresponding distance is calculated from the known wavelength for the system. That is, by multiplying the number of wavelengths 'N' by the period of a single wavelength at said second frequency. The round trip distance is divided by two to obtain the actual thickness of the work piece 20.

As an example, assume that the work piece 20 is a section of Zerodur, which supports a sonic velocity of 7600 m/s. First, a phase null is found at 24.984252 Mhz. This corresponds to an integral number of wavelengths in the round trip measuring path. Next, the frequency is raised until the next null is found at a frequency of 25.059055 Mhz. The frequency difference expressed as a fraction of the original frequency is:

$$\Delta f/f = (f_2 - f_1)/f_1 \quad [1]$$
$$= (25.059055 - 24.984252)/24.984252$$
$$= 1/334$$
$$= 1/N$$

indicating 334 wavelengths in the path. Using c=7600 m/s as the velocity of sound in this medium, the length of the initial wavelength is:

$$c/f = 7600/24.984252E06 = 304.191616 \text{ microns}. \quad [2]$$

Multiplying by the 334 wavelengths gives:

$$334 * 303.191616 = 101600 \text{ microns}$$

for the round trip or 2 inches for the sample thickness.

In an alternative mode of operation, a change in thickness of a work piece due to a machining operation may be determined utilizing the system of the present invention. In this mode, the frequency is set to a phase null. Next, the machining operation is performed. Then, the frequency is raised to the next null, restoring the same number of (shortened) wavelengths to the path. The fractional change in frequency, calculated by dividing the frequency change by the frequency at the first null, is also the fractional change in material thickness. The actual change in thickness is obtained by multiplying the fractional change by the original thickness of the work piece as determined by the method given above or by simple mechanical or other gaging. Accurate knowledge of this thickness is not required. The fractional error appears as a corresponding fraction of reading, not of full scale.

For example, as in the former example, assume that the work piece 20 is a section of Zerodur, which supports a sonic velocity of 7600 m/s. First, a phase null is found at 24.984252 Mhz where exactly 334 wavelengths fit the 101,600 micron (4 inch) round trip path. Next, a micron of material is removed, shortening the round trip path by 2 microns to 101,598 microns, a length which will no longer contain 334 wavelengths at the above frequency. The phase detector output is no longer null. Finally, the frequency is raised to 24.984744 Mhz so that 334 (shorter) wavelengths again fill the measuring path. The frequency change is 24,984,744−24,984,252=Δf=492 hertz, a figure easily measured by conventional means. The fractional change Δf/f is $$1.969202E\text{-}05 * 1.1016E05 = 2.00 \text{ microns}$$

which when divided by 2 for the round trip gives the correct result, 1 micron. The estimate of the initial thickness of the work piece can be obtained from such sources as mechanical or optical gaging, and need not be very accurate. The percent error in this initial determination appears as an equal percent-of-measurement error, not as percent of full scale. Thus, an error of −10 percent in the initial dimension of 2 inches would cause a measurement of 0.9 microns instead of 1 micron.

In yet a third mode of operation, the operating frequency is cyclically swept through the measuring frequency range while the output of the phase detector is observed. The phase detector, then, will produce a periodic waveform having zeros at the phase-null points. The phase of the detected waveform with respect to that of the original sweeping control signal is the range or thickness output desired.

Although the foregoing measuring system has exploited the colinearity of the multiple received echoes at successive occurrences of 360 degrees phase shift, a similar colinearity occurs at 180 degrees, and the resulting 180 degree occurrences can likewise be used as measuring points, either alone or in alternation with the 360 degree points. Thus, the measuring frequency may be gradually increased between successive 180 degree and 360 degree points, noting the frequency at which these occur. A computation in accordance with the above-teachings will yield the work piece thickness. In this case, the measuring points correspond to the occurrence of integral numbers of half-wavelengths in the round-trip path.

The use of alternating points as described above, may be advantageous in requiring a smaller frequency excursion. In addition, the type of phase detector available must also be considered, i.e., one having a 360 degree range versus one having a 180 degree range.

Thus, the present invention has been described herein with reference to a particular embodiment for a particular application. Those having ordinary skill in the art and access to the present teachings will recognize additional modifications applications and embodiments within the scope thereof. For example, the invention is not limited to in an acoustic system. The teachings of the present invention may be utilized with other technologies such as laser radar by way of example.

It is therefore intended by the appended claims to cover any and all such applications, modifications and embodiments within the scope of the present invention.

Accordingly,

What is claimed is:

1. A system for measuring the thickness of an element comprising:

first means for transmitting a first signal of energy of a first phase into said element;

second means for receiving a second signal, said second signal being a reflection of said first signal from a distal surface of said element;

third means for comparing a phase of said second signal to the phase of said first signal to determine a phase difference therebetween, and outputting a third signal representing the phase difference; and fourth means for processing said third signal to determine the thickness of said element said fourth means further comprising:

means for adjusting the frequency of said first signal until a second frequency is reached at which said phase difference goes substantially to zero to identify a first null and an integral number of wavelengths in a round trip path comprising the paths of said first and second signals;

means for gradually changing the frequency of said first signal by an amount of frequency change Δf to create a second null indicating an increase by one in the number of wavelengths in said round trip path:

means for calculating the number of wavelengths in the round trip path N at said second frequency by dividing the second frequency f by said amount of frequency change Δf;

means for calculating a round trip distance along the round trip path through said element by multiplying the number of wavelengths N by the length of a single wavelength at said second frequency; and means for calculating the thickness of said element by dividing said round trip distance by two.

2. The invention of claim 1 wherein said first signal is an acoustic signal.

3. The invention of claim 2 wherein said first means includes a transducer.

4. The invention of claim 3 wherein said first means includes a frequency synthesizer for applying said first signal to said transducer.

5. The invention of claim 4 wherein said second means includes said transducer and a directional coupler connected to said transducer to receive said second signal reflected from a distal surface of said element.

6. The invention of claim 5 wherein said third means includes a phase detector for determining the phase shift between said first and second signals and outputting said third signal representing the phase shift.

7. A method for measuring the thickness of an element including the steps of:

applying a first signal of energy of a first phase and a first frequency f to said element;

receiving a second signal, said second signal being a reflection of said first signal from a distal surface of said element;

comparing a phase of said second signal to the phase of said first signal to determine the phase difference therebetween, and outputting a third signal representing the phase difference;

adjusting the frequency of said first signal until a second frequency is reached at which said phase difference goes substantially to zero to identify a first null and an integral number of wavelengths in a round trip path comprising the paths of said first and second signals;

gradually changing the frequency of said first signal by an amount of frequency change Df to create a second null indicating an increase by one in the number of wavelengths in said round trip path;

calculating the number of wavelengths in the round trip path N at said second frequency by dividing the second frequency f by said amount of frequency change Df;

calculating a round trip distance along the round trip path through said element by multiplying the number of wavelengths N by the length of a single wavelength at said second frequency; and calculating the thickness of said element by dividing said round trip distance by two.

* * * * *